Figures 1A, 1B:
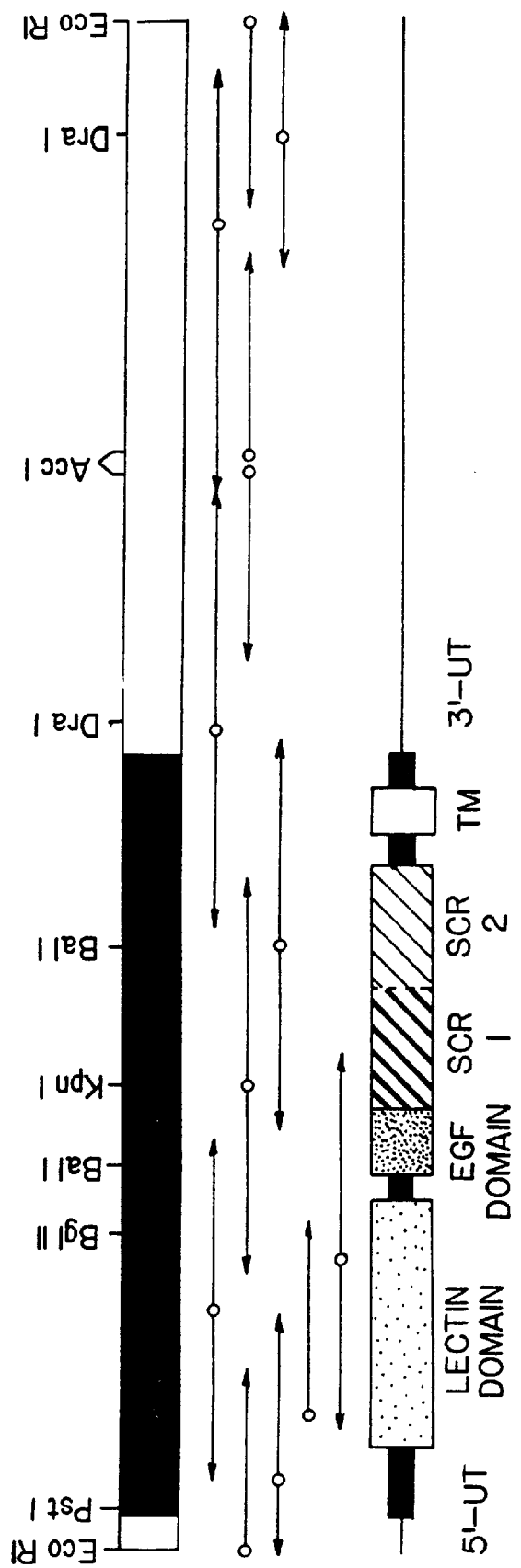

US005830471A

United States Patent [19]
Tedder

[11] Patent Number: 5,830,471
[45] Date of Patent: Nov. 3, 1998

[54] METHODS AND COMPOSITIONS COMPRISING ANTI-LAM-1 ANTIBODIES

[75] Inventor: Thomas F. Tedder, Wellesley, Mass.

[73] Assignee: Dana-Farber Cancer Institute, Boston, Mass.

[21] Appl. No.: 459,097

[22] Filed: Jun. 2, 1995

Related U.S. Application Data

[62] Division of Ser. No. 983,606, Nov. 30, 1992, which is a continuation of Ser. No. 730,503, Jul. 8, 1991, abandoned, which is a continuation of Ser. No. 313,109, Feb. 21, 1989, abandoned.

[51] Int. Cl.⁶ .................... A61K 39/395; G01N 33/53; C07K 16/28
[52] U.S. Cl. .................... 424/139.1; 424/141.1; 424/144.1; 424/153.1; 424/173.1; 435/7.1; 435/7.24; 530/387.9; 530/388.2; 530/388.22; 530/388.7; 530/388.73; 530/388.75; 530/388.85; 530/389.6
[58] Field of Search .................... 530/387.9, 388.2, 530/388.22, 388.7, 389.1, 389.6, 388.73, 388.75, 388.85; 435/70.21, 172.2, 240.27, 7.24, 7.1; 424/139.1, 144.1, 153.1, 173.1, 141.1

[56] References Cited

U.S. PATENT DOCUMENTS

| | | | |
|---|---|---|---|
| 4,783,330 | 11/1988 | Furie et al. | 424/1.1 |
| 4,835,255 | 5/1989 | Weissman et al. | 530/350 |
| 5,026,537 | 6/1991 | Daddona et al. | 424/1.1 |
| 5,098,833 | 3/1992 | Lasky et al. | 435/69.1 |
| 5,216,131 | 6/1993 | Lasky et al. | 530/350 |
| 5,227,369 | 7/1993 | Rosen et al. | 514/23 |

OTHER PUBLICATIONS

Capon, D.J. et al., "Designing CD4 Immunoadhesions for AIDS Therapy," *Nature* 337, pp. 525–531 (1989).
Harlow, E. and D. Lane, *Antibodies: A Laboratory Manual*, Cold Spring Harbor Laboratory (1988), p. 287.
Aizawa et al., "Molecular basis of the recognition of intraveneously transplanted hemopoietic cells by bone marrow," Proc. Natl. Acad. Sci. USA 85:3180–3183 (1988).
Bargatze et al., "High Endothelial Venule Binding as a Predictor of the Dissemination of Passaged Murine Lymphomas," J. Exp. Med. 166:1125–1131 (1987).
Berg et al., "Homing Receptors and Vascular Addressins: Cell Adhesion Molecules that Direct Lymphocyte Traffic," Immunol. Rev. 108:421–427 (1989).
Bevilacqua et al., "Endothelial Leukocyte Adhesion Molecule 1: An Inducible Receptor for Neutrophils Related to Complement Regulatory Proteins and Lectins," Science 243:1160–1165 (1989).
Bevilacqua et al., "Identification of an inducible endothelial–leukocyte adhesion molecule," Proc. Natl. Acad. Sci. USA 84:9238–9242 (1987)*.
Bowen et al., "Characterization of a Human Homologue of the Murine Peripheral Lymph Node Homing Receptor," J. Cell Biol. 109:421–427 (1989)*.

Butcher et al., "Lymphocyte Adherence to High Endothelial Venules: Characterization of a Modified In Vitro Assay, and Examination of the Binding of Syngenic and Allogenic Lymphocyte Populations," J. Immunol. 123:1996–2003 (1979).
Camerini et al., "Leu–8/TQ–1 is the human equivalent of the Mel–14 lymph node homing receptor," Nature 342:78–82 (1989).
Carbone et al. "Expression of Leu–8 Surface Antigen in B–Cell Lymphomas. Correlation with Other B–Cell Markers," J. Pathol. 154:133–140 (1988).
Chin et al., "Lymphocyte Recognition of Lymph Node High Endothelium. I. Inhibition of In Vitro Binding by a Component of Thoracic duct Lymph," J. Immunol. 125:1764–1769 (1980).
Chin et al., "Lymphocyte Recognition of Lymph Node High Endothelium. II. Characterization of an In Vitro Inhibitory Factor Isolated by Antibody Affinity Chromatography," J. Immunol. 125:1770–1774 (1980).
Chin et al., "Lymphocyte Recognition of Lymph Node High Endothelium. V. Isolation of Adhesion Molecules from Lysates of Rat Lymphocytes," J. Immunol. 131:1368–1374 (1983).
Collins et al., "Structure and Chromosomal Location of the Gene for Endothelial–Leukocyte Adhesion Molecule 1," J. biol. chem. 266:2466–2473 (1991).
Dana et al., "Two Functional Domains in the Phagocyte Membrane Glycoprotein Mo1 Identified with Monoclonal Antibodies," J. Immunol. 137:3259–3263 (1986).
DiStefano et al., "Identification of a truncated form of the nerve growth factor receptor," Proc. Natl. Acad. Sci. USA 85:270–274 (1988).
Dowbenko et al., "Characterization of the Murine Homing Receptor Gene Reveals Correspondence between Protein Domains and coding Exons," Genomics 9:270–277 (1991).
Downing et al., "Ligand and Protein Kinase C Downmodulate the Colony Stimulating Factor 1 Receptor by Independent Mechanisms," Mol. cell. Biol. 9:2890–2896 (1989).
Drickamer et al., "Complete amino acid sequence of a membrane receptor for glycoproteins," J. Biol. Chem. 256:5827–5839 (1981)*.
Drickamer et al., "Two Distinct Classes of Carbohydrate–recognition Domains in Animal Lectins," J. Biol. Chem. 263:9557–9560 (1988)*.

(List continued on next page.)

*Primary Examiner*—Toni R. Scheiner
*Assistant Examiner*—Nancy A. Johnson
*Attorney, Agent, or Firm*—Fish & Neave; James F. Haley, Jr., Esq.; Jane T. Gunnison, Esq.

[57] ABSTRACT

Human lymphocyte-associated cell surface protein LAM-1, which includes domains homologous with binding domains of animal lectins, growth factors, and C3/C4 binding proteins, and the cDNA encoding LAM-1, are described. Antagonists to LAM-1 are used in a method of treating a human patient suffering from a lymphocyte-mobilizing condition which involves administering a therapeutic amount of the antagonist in a non-toxic pharmaceutical carrier substance.

2 Claims, 6 Drawing Sheets

OTHER PUBLICATIONS

Duijvestijn et al., "Mechanisms and regulation of lymphocyte migration," Immunol. today 10:23–28 (1989).
Ezekowitz et al., "A human mannose–binding protein is an acute–phase reactant that shares sequence homology with other vertebrate lectins," J. Exp. Med. 167:1034–1046 (1988)*.
Gallatin et al., "Lymphocyte Homing Receptors," Cell 44:673–680 (1986).
Gallatin et al., "A cell–surface molecule involved in organ–specific homing of lymphocytes," Nature 304:30–34 (1983).
Gatenby et al., "Dissection of Immunoregulatory Subpopulations of T Lympohocytes within the Helper and Suppressor Sublineages in Man," J. Immunol. 129:1997–2000 (1982)*.
Geng et al. "Rapid neutrophil adhesion to activated endothelium mediated by GMP–140," Nature 323:757–760 (1990).
Goldstein et al., "A Human Lymphocyte Homing Receptor, the Hermes Antigen, is Related to Catilage Preteoglycan Core and Link Proteins," Cell 56:1063–1072 (1989).
Gregory, "Isolation and structure of urogastrone and its relationship to epidermal growth factor," Nature 257:325–327 (1975)*.
Griffin et al., "Granulocyte–Macrophage Colony–Stimulating Factor and Other Cytokines Regulate Surface Expression of the Leukocyte Adhesion Molecule–1 on Human Neutrophils, Monocytes, and their Precursors," J. Immunol. 145:576–584 (1990)*.
Hallmann et al., "The peripheral lymph node homing receptor, LECAM–1, is involved in CD18–independent adhesion of human neutrophils to endothelium," Biochem. Biophys. Res. Comm. 174:236–243 (1991).
Hidaka et al., "Isoquinolinessulfonamides, Novel and Potent Inhibitors of Cyclic Nucleotide Dependent Protein Kinase and Protein Kinace C," Biochemistry 23:5036–5041 (1984).
Hildreth et al., "The Human Lymphocyte Function–Associated (HFLA) Antigen and a Related Macrophage Differentiation Antigen HMac–1): Functional Effects of Subunit–Specific Monoclonal Antibodies," J. Immunol. 134:3272–3280 (1985).
Ichinose et al., "Amino–Acid Sequence of the b Subunit of Human Factor XIII, a Protein Composed of Ten Repetitive Segments," Biochemistry 25:4633–4638 (1986)*.
Imai et al., "Identification of a carbohydrate–based endothelial ligand for a lymphocyte homing receptor," J. Cell Biol. 113:1213–1221 (1991).
Jalkanen et al., "Lymphocyte Recognition of High Endothelium: Antibodies to Distinct Epitopes of an 85–95–kD Glycoprotein Antigen Differentially Inhibit Lymphocyte Binding to Lymph Node, Mucosal, or Synovial Endothelial Cells," J. Cell Biol. 105:983–990 (1987).
Johnson, G.J., et al., "Thromboxane unresponsive dog platelets have an abnormal thromboxane $A_2$/prostaglandin $H_2$ receptor–linked G protein," Blood Suppl. 72:327A (1988)*.
Johnston, G.I., et al., "Cloning of GMP–140, a Granule Membrane Protein of Platelets and Endothelium: Sequence Similarity to Proteins Involved in Cell Adhesion and Inflammation," Cell 56:1033–1044 (1989)*.
Johnston, G.I., et al., "Structure of the Human Gene Encoding Granule Membrane Protein–140, a Member of the Selectin Family of Adhesion Receptors for Leukocytes," J. Biol. Chem. 265:21381–21385 (1990).

Jung et al., "Rapid Modulation of Homing Receptors ($gp90^{MEL-14}$) induced by Activators of Protein Kinase C," J. Immunol. 144:130–136 (1990).
Jutila et al., "Characterization of a Functionally Important and Evolutionarily Well–Conserved Epitope Mapped to the Short Consensus Repeats of E–Selectin and L–Selectin," J. Exp. Med. 175:1565–1573 (1992).
Jutila et al., "Function and Regulation of the Neutrophil MEL–14 Antigen In Vivo: Comparison with LFA–1 and MAC–1," J. Immunol. 143:3318–3324 (1989).
Kanof et al., "Leu–8 Antigen Expression is Diminished During Cell Activation But Does Not Correlate with Effector Function of Activated T Lymphocytes," J. Immunol. 140:3701–3706 (1988).
Kansas et al., "Molecular Mapping of Functional Domains of the Leukocyte Receptor for Endothelium, LAM–1," J. Cell Biol. 114:351–358 (1991)*.
Kansas et al., "Expression of Adhesion Structures During B Cell Development in Man," J. Immunol. 142:3058–3062 (1989).
Kansas et al., "A Family of Cell–Surface Glycoproteins Defined by a Putative Anti–Endothelial Cell Receptor Antibody in Man," J. Immunol. 142:3050–3057 (1989).
Kansas et al., "Maturational and Functional Diversity of Human B Lymphocytes Delineated with Anti–Leu–8," J. Immunol. 134:3003–3006 (1985).
Kikutani et al., "Molecular Structure of Human Lymphocyte Receptor for Immunoglobulin E," Cell 47:657–665 (1986)*.
Kishimoto et al., "Antibodies Against Human Neutrophil LECAM–1 (LAM–1/Leu–8/DREG–56 Antigen) and Endothelial Cell ELAM–1 Inhibit a Common CD18–Independent Adhesion Pathway In Vitro," Blood 78:805–811 (1991).
Kishimoto et al., "Identification of a Human Peripheral Lymph Node Homing Receptor: A Rapidly Down–Regulated Adhesion Molecule", Proc. Natl. Acad. Sci. USA 87:2244–2248 (1990)*.
Kishimoto et al., "Neutrophil Mac–1 and MEL–14 Adhesion Proteins Inversely Regulated by Chmotactic Factors," Science 245:1238–1241 (1989).
Klickstein et al., "Human C3b/C4b Receptor (CR1): Demonstration of Long Homologous Repeating Domains That Are Composed of the Short Consensus Repeats Characteristic of C3/C4 Binding Proteins," J. Exp. Med. 165:1095–1112 (1987).
Kozak et al., "Point Mutations Define a Sequence Flanking the AUG Initiator Codon That Modulates Translation by Eukaryotic Ribosomes," Cell 44:283–292 (1986)*.
Krusius et al., "A Fibroblast Chondroitin Sulfate Proteoglycan Core Protein Contains Lectin–like and Growth Factor–like Sequences," J. Biol. Chem. 262:13120–13125 (1987)*.
Kurk et al., "Characterization of an Endothelial Cell Antigen Recognized by an Anti–Leukocyte Homing Receptor (L–Selectin) Monoclonal Antibody," FASEB J. 6:A1192 (1992).
Larsen et al., "PADGEM–Dependent adhesion of platelets to monocytes and neutrophils is mediated by a lineage–specific carbohydrate," LNF III (CD15), Cell 63:467–474 (1990).
Larsen et al., "PADGEM Protein: A receptor that mediates the Interaction of activated platelets with neutrophils and monocytes," Cell 59:305–312 (1989).
Lasky et al., "Cloning of a Lymphocyte Homing Receptor Reveals a Lectin Domain," Cell 56:1045–1055 (1989).
Lasky, "Selectins: Interpreters of Cell–Specific Carbohydrates Information During Inflammation," Science 258:964–969 (1992)*.

Leonard et al., "Molecular cloning and expression of cDNAs for the human interleukin–2 receptor," Nature 311:626–631 (1984)*.

Lewinsohn et al., "Leukocyte–endothelial cell recognition: Evidence of a common molecular mechanism shared by neutrophils, lymphocytes, and other leukocytes," J. Immunol. 138:4313–4321 (1987).

Ley et al., "Lectin–Like Cell Adhesion Molecule 1 Mediates Leukocyte Rolling in Mesenteric Venules In Vivo," Blood 77:2553–2555 (1991).

Luscinskas et al., "Cytokine–activated human endothelial monolayers support enhanced neutrophil transmigration via a mechanism involving both endothelial–leukocyte adhesion molecule–1 and intercellular adhesion molecule–1," J. Immunol. 146:1617–1625 (1989).

Luscinskas et al., "Endothelial–leukocyte adhesion molecule–1–dependent and leukocyte (CD11/CD18)–dependent mechanisms contribute to polymorphonuclear leukocyte adhesion to cytokine–activated human vascular endothelium," J. Immunol. 142:2257–2263 (1989).

Marx, "New Family of Adhesion Proteins Discovered," Science 243:1144 (1989)*.

Michie et al., "Expression of the Leu–8 Antigen by B–Cell Lymphomas," Am. J. Clin. Pathol. 88:486–490 (1987).

Miyake et al., "Hyaluronate Can Function as a Cell Adhesion Molecule and CD44 Participates in Hyaluronate Recognition," J. Exp. Med. 172:69–75 (1990).

Morley et al., "Internal homologies of the Ba fragment from human complement component Factor B, a class III MHC antigen," EMBO J. 3:153–157 (1984)*.

Nojima et al., "VLA–4 Mediates CD3–dependent CD4$^+$ T Cell Activation Via the CS1 Alternatively Spliced Domain of Fibronectin," J. Exp. Med. 172:1185–1192 (1990).

Ord et al., "Structure of the Gene Encoding the Human Leukocyte Adhesion Molecule–1 (TQ1, Leu–8) of Lymphocytes and Neutrophils," J. Biol. Chem. 265:7760–7767 (1990)*.

Osborn, "Leukocyte Adhesion to Endothelium in Inflammation," Cell 62:3–6 (1990)*.

Pals et al., "Expression of Lymphocyte Homing Receptor as a Mechanism of Dissemination in Non–Hodgkin's Lymphoma," Blood 73:885–888 (1989).

Picker et al., "The Neutrophil Selectin LECAM–1 Presents Carbohydrate Ligands to the Vascular Selectins ELAM–1 and GMP–140," Cell 66:921–933 (1991).

Polte et al., "Full length vascular cell adhesion molecule 1 (VCAM–1)," Nuc. Acids Res. 18:5901 (1990).

Porteau et al., "Shedding of Tumor Necrosis Factor Receptors by Activated Human Neutrophils," J. Exp. 172:599–607 (1990).

Reinherz et al., "Heterogeneity of Human T4 Inducer T Cells Defined by a Molecular Antibody that Delineates Two Functional Subpopulations," J. Immunol. 128:463–468 (1982)*.

Rice et al., "Vascular and Nonvascular Expression of INCAM–110," Amer. J. Pathol. 138:385–393 (1991).

Rice et al., "An Inducible Endothelial Cell Surface Glycoprotien Mediates Melanoma Adhesion," Science 246:1303–1306 (1989).

Rosen et al., "Involvement of Sialic Acid on Endothelial Cells in Organ–Specific Lymphocyte Recirculation," Science 228:1005–1007 (1985).

Rothlein et al., "A Human Intercellular Adhesion Molecular (ICAM–1) Distinct From LFA–1," J. Immunol. 137:1270–1274 (1986).

Rothlein et al., "A Form of Circulating ICAM–1 in Human Serum," J. Immunol. 147:3788–3793 (1991).

Sanchez–Madrid et al., "Three distinct antigens associated with human T–lymphocyte–mediated cytolysis: LFA–1, LFA–2, and LFA–3," Proc. Natl. Acad. Sci. USA 79:7489–7493 (1982).

Sher et al., "Homing Receptors and Metastasis," Adv. Can. Res. 51:361–389 (1988).

Siegelman et al., "The mouse lymph node homing receptor is identical with the lymphocyte cell surface marker Ly–22: Role of the EGF domain in endothelial binding," Cell 61:611–622 (1990).

Siegelman et al., Human homologue of mouse lymph node homing receptor: Evolutionary conservation at tandem cell interaction domains, Proc. Natl. Acad. Sci. USA 86:5562–5566 (1989).

Siegelman et al., "Mouse Lymph Node Homing Receptor cDNA Clone Encodes a Glycoprotein Revealing Tandem Interactions Domains," Science 243:1165–1172 (1989)*.

Smith et al., "Chemotactic factors regulate lectin adhesion molecule 1 (LECAM–1)–dependent neutrophil adhesion to cytokine–stimulated endothelial cells In Vitro," J. Clin. Invest. 87:609–618 (1991).

Spertini et al., "Function and Evolutionary Conservation of Distinct Epitopes on the Leukocyte Adhesion Molecule–1 (TQ–1, Leu–8) that Regulate Leukocyte Migration," J. Immunol. 147:942–949 (1991)*.

Spertini et al., "Leukocyte Adhesion Molecule (LAM–1, L–Selectin) Interacts with an Inducible Endothelial Cell Ligand to Support Leukocyte Adhesion," J. Immunol. 147:2565–2573 (1991)*.

Spertini et al., "Regulation of Leukocyte Adhesion Molecule–1 (TQ1, Leu–8) Expression and Shedding by Normal and Malignant Cells," Leukemia 5:300–308 (1991)*.

Spertini et al., "Regulation of leukocyte migration by activation of the leukocyte adhesion molecule–1 (LAM–1) selectin," Nature 349:691–694 (1991)*.

Spiess et al., "Sequence of a Second Human Asialoglycoprotein Receptor: conservation of Two Receptor Genes During Evolution," Proc. Natl. Acad. Sci. USA 82:6465 6469 (1985)*.

Springer, "Adhesion receptors of the immune system," Nature 346:425–434 (1990).

Stamekovic et al., "A Lymphocyte Molecule Implicated in Lymph Node Homing is a Member of the Cartilage Link Protein Family," Cell 56:1057–1062 (1989).

Stamper et al., "Lymphocyte Homing into Lymph Nodes: In Vitro Demonstration of the Selective Affinity of Recirculating Lymphocytes for High–Endothelial Venules," J. Exp. Med. 144:828–833 (1976).

Stoolman et al., "Horning Receptors on Human and Rodent Lymphocytes–Evidence for a Conserved Carbohydrate–Binding Specificity," Blood 70:1842–1850 (1987).

Stoolman, "Adhesion Molecules Controlling Lymphocyte Migration," Cell 56:907–910 (1989)*.

Stoolman et al., "Phosphomannosyl Receptors May Participate in the Adhesive Interaction between Lymphocytes and High Endothelial Venules," J. Cell Biol. 99:1535–1540 (1984).

Stoolman et al., "Adhesion Molecules of Cultured Hematopoietic Malignancies," J. Clin. Invest. 84:1196–1205 (1989).

Strickler et al., "Intermediate Lymphocytic Lymphoma: An Immunophenytypic Study with Comparison to Small Lymphocytic Lymphoma and Diffuse Small Cleaved Cell Lymphoma," Hum. Path. 19:550–554 (1988).

Takahashi et al., "Cloning and Sequencing of cDNA of *Sarcophaga perengrina* Humoral Lectin Induced on Injury of the Body Wall," J. Biol. Chem. 260:12228–12233 (1985).

Tamaoki et al., "Staurosporine, A Potent Inhibitor of Phospholipid/Ca$^{++}$ Dependent Protein Kinase," Biochem. Biophys. Res. Comm. 135:397–402 (1986).

Tedder, "Cell–surface Receptor Shedding: A Means of Regulating Function," Am. J. Respir. Cell Mol. Biol. 5:305–307 (1991).

Tedder et al., "Function of the LFA–1 and T4 molecules in the direct activation of resting human B lymphocytes by T lymphocytes," Eur. J. Immunol. 16:1539–1543 (1986).

Tedder et al., "Human antigen–specific memory T cells express the homing receptor (LAM–1) necessary for lymphocyte recirculation," Eur. J. Immunol. 20:1351–1355 (1990)*.

Tedder et al., "Isolation and Chromosomal Localization of cDNAs Encoding a Novel Human Lymphocyte Cell Surface Molecule, LAM–1," 170:123–133 (1980).

Tedder et al., "Human Lymphocytes Differentiation Antigens HB–10 and HB–11," J. Immunol. 134:2989–2994 (1985)†.

Tedder et al., "Expression of the Human Leukocyte Adhesion Molecule, LAM–1: Identity with the TQ1 and Leu–8 Differentiation Antigens," J. Exp. Med. J. Immunol. 144:532–540 (1990)*.

Tedder et al., "Heterogeneity in the B1 (CD20) Cell Surface Molecule Expressed by Human B–Lymphocytes," Molecular Immunol. 25:1321–1330 (1988).

Tedder et al., "Isolation and structure of a cDNA encoding the B1 (CD20) cell–surface antigen of human B lymphocytes," Proc. Natl. Acad. Sci. USA 85:208–212 (1988)*.

True et al., "Requirement for Sialic Acid on the Endothelial Ligand of a Lymphocyte Homing Receptor," J. Cell Biol. 111:2757–2764 (1990).

von Haijne, "A New Method for Predicting Signal Sequence Cleavage Sites," Nucleic Acid Research 14:4683–4690 (1986)*.

Walcheck et al., "Characterization of the Bovine Peripheral Lymph Node Homing Receptor: A Lectin Cell Adhesion Molecule (LECAM)," Eur. J. Immunol. 22:469–476 (1992).

Watson, M. et al., "Genomic Organization of the Selectin Family of Leukocyte Adhesion Molecules on Human and Mouse Chromosome 1", J. Exp. Med. 172:263–272 (1990).

Watson, S. et al., "A Homing Receptor–IgG Chimera as a Probe for Adhesive Ligands of Lymph Node High Endothelial Venules," J. Cell Biol. 110:2221–2229 (1990).

Watson, S. et al., "The complement binding–like domains of the murine homing receptor facilitate lectin activity," J. Cell Biol. 115:235–243 (1991).

Watson, S. et al., "Neutrophil influx into an inflammatory site inhibited by a soluble homing receptor–IgG chimera," Nature 349:164–167 (1991).

Weiss et al., "Interactions of cancer cells with the microrvasculature during metastasis," FASEB J. 2:12–21 (1988).

Wu et al., "Evolutionary Conservation of Tissue–specific Lymphocyte–Endothelial Cell Recognition Mechanisms Involved in Lymphocyte Homing," J. Cell Biol. 107:1845–1851 (1988)*.

Yednock et al., "Phosphomannosyl–derivatized Beads Detect a Receptor Involved in Lymphocyte Homing," J. Cell Biol. 104:713–723 (1987).

Yednock et al., "Receptors Involved in Lymphocyte Homing: Relationship between a Carbohydrate–binding Receptor and the MEL–14 Antigen," J. Cell Biol. 104:725–731 (1987).

Yoshitake et al., "Nucleotide Sequence of the Gene for Human Factor IX (Antihemophilic Factor B)," Biochemistry 25:3736–3750 (1985)*.

J.D. Mountz et al., "Prevention of Lymphadenopathy In MRL–1pr/1pr Mice By Blocking Peripheral Lymph Node Homing With Mel–14 In Vivo," *J. Immunol.,*140, pp. 2943–2949 (1988).

Reeck et al., Cell 50:667, 1987.

Harris, TIBTECH 11:42–44, 1993.

FIG. 2A

```
                                                                          1
                                                                          M   G
gaattcCCCTTT GGGCAAGGAC CTGAGACCCT TGTGCTAAGTCAAGAGGCTCA ATG GGC C   R   R   T   R   E   G   P   S   K   A   M
TGC AGA AGA ACT AGA GAA GGA CCA AGC AAA GCC ATG                          94
                             10                  
                                             30
 I   F   P   W   K   C   Q   T   Q   R   D   L   W   N   I
ATA TTT CCA TGG AAA TGT CAG AGC ACC CAG AGG GAC TTA TGG AAC ATC
             20

F   K   L   W   G   W   T   M   L   C   C   D
TTC AAG TTG TGG GGG TGG ACA ATG CTC TGT TGT GAT                          168
                             40
                                         →
 F   L   A   H   H   G   T   D   C   W   T   Y   H   Y   S   E
TTC CTG GCA CAT CAT GGA ACC GAC TGC TGG ACT TAC CAT TAT TCT GAA
                             50

K   P   M   N   W   Q   R   A   R   R   F   C   I   Q   N   K   A   E   I
AAA CCC ATG AAC TGG CAA AGG GCT AGA AGA TTC TGC ATA CAA AAC AAG GCG GAA ATT  262
         60                          70                      80

R   D  | N   Y   T | D   L   V   A   F   P   F   S   R   S
CGA GAC | AAT TAC ACA| GAT TTA GTT GCC TTT CCT TTC AGT CGT TCT               346
                 90

E   Y   L   E   K   T   L
GAG TAT CTG GAG AAG ACT CTG
```

```
            100                                                110
    Y    Y    W    I    G    I    R    K    I    G    G    I    W    T    W
   TAC  TAC  TGG  ATA  GGA  ATC  CGG  AAG  ATA  GGA  GGA  ATA  TGG  ACG  TGG
                                 120
    V    G    T   |N    K    S|   L    T    E    E    A    E    N
   GTG  GGA  ACC |AAC  AAA  TCT| CTC  ACT  GAA  GAA  GCA  GAG  AAC   430
                  130                                            140
    W    G    D    G    E    P    N    N    K    K    N    K    E    D    C
   TGG  GGA  GAT  GGT  GAG  CCC  AAC  AAC  AAG  AAG  AAC  AAG  GAG  GAC  TGC
                                      150
    V    E    I    Y    I    K    R    N    K    D    A    G    K
   GTG  GAG  ATC  TAT  ATC  AAG  AGA  AAC  AAA  GAT  GCA  GGC  AAA   514
                            160
    W    N    D    D    A    C    H    K    L    K    A    A    L    C    Y
   TGG  AAC  GAT  GAC  GCC  TGC  CAC  AAA  CTA  AAG  GCA  GCC  CTC  TGT  TAC
   170                                                 180
    T    A    S    C    Q    P    W    S    C    S    G    H    G
   ACA  GCT  TCT  TGC  CAG  CCC  TGG  TCA  TGC  AGT  GGC  CAT  GGA   598
                                      190
    E    C    V    E    I    I    N   |N    Y    T|   C    N    C    D    V
   GAA  TGT  GTA  GAA  ATC  ATC  AAT |AAT  TAC  ACC| TGC  AAC  TGT  GAT  GTG
              200                                                210
    G    Y    Y    G    P    Q    C    Q    F    V    I    Q    C
   GGG  TAC  TAT  GGG  CCC  CAG  TGT  CAG  TTT  GTG  ATT  CAG  TGT   682
                                                220
    E    P    L    E    A    P    E    L    G    T    M    D    C    T    H
   GAG  CCT  TTG  GAG  GCC  CCA  GAG  CTG  GGT  ACC  ATG  GAC  TGT  ACT  CAC
                            230
    P    L    G    N    F    N    F    N    S    Q    C    A    F
   CCT  TTG  GGA  AAC  TTC  AAC  TTC  AAC  TCA  CAG  TGT  GCC  TTC   766
   240                                                 250
    S    C    S    E    G    T   |N    L    T|   G    I    E    E    T    T
   AGC  TGC  TCT  GAA  GGA  ACA |AAC  TTA  ACT| GGG  ATT  GAA  GAA  ACC  ACC
                                 260
    C    E    P    F    G   |N    W    S|   S    P    E    P    T
   TGT  GAA  CCA  TTT  GGA |AAC  TGG  TCA| TCT  CCA  GAA  CCA  ACC   850
                            270                                 280
    C    Q    V    I    Q    C    E    P    L    S    A    P    D    L    G
   TGT  CAA  GTG  ATT  CAG  TGT  GAG  CCT  CTA  TCA  GCA  CCA  GAT  TTG  GGG
                                                290
    I    M   |N    C    S|   H    P    L    A    S    F    S    F
   ATC  ATG |AAC  TGT  AGC| CAT  CCC  CTG  GCC  AGC  TTC  AGC  TTT   934
                                 300
    T    S    A    C    T    F    I    C    S    E    G    T    E    L    I
   ACC  TCT  GCA  TGT  ACC  TTC  ATC  TGC  TCA  GAA  GGA  ACT  GAG  TTA  ATT
   310                                                 320
    G    K    K    K    T    I    C    E    S    S    G    I    W
   GGG  AAG  AAG  AAA  ACC  ATT  TGT  GAA  TCA  TCT  GGA  ATC  TGG  1018
                                      330
    S   |N    P    S|   P    I    C    Q    K    L    D    K    S    F    S
   TCA |AAT  CCT  AGT| CCA  ATA  TGT  CAA  AAA  TTG  GAC  AAA  AGT  TTC  TCA
         340                                                 350
    M    I    K    E    G    D    Y    N    P    L    F    I    P
   ATG  ATT  AAG  GAG  GGT  GAT  TAT  AAC  CCC  CTC  TTC  ATT  CCA  1102
```

FIG. 2B

```
              V   A   V   M   V   T   A   F   S   G   L   A   F   I   I
                                      360
             GTG GCA GTC ATG GTT ACT GCA TTC TCT GGG TTG GCA TTT ATC ATT
                                  370
              W   L   A   R   R   L   K   K   G   K   K   S   K
             TGG CTG GCA AGG AGA TTA AAA AAA GGC AAG AAA TCC AAG          1186
                  380
              R   S   M   N   D   P   Y   *
             AGA AGT ATG AAT GAC CCA TAT TAA ATCGCCCTTG GTGAAAGAAA

ATTCTTGGAA TACTAAAAAT CATGAGATCC TTTAAATCCT TCCATGAAAC                    1280
GTTTTGTGTG GTGGCACCTC CTACGTCAAA CATGAAGTGT GTTTCCTTCA
GTGCATCTGG GAAGATTTCT ACCTGACCAA GAGTTCCTTC AGCTTCCATT                    1380
TCACCCCTCA TTTATCCCTC AACCCCAGC CCACAGGTCT TTATACAGCT
CAGCTTTTTC TCTTTTCTGA GGAGAAACAA ATAACACCAT AAAGGGAAAG                    1480
GATTCATGTG GAATATAAAG ATGGCTGACT TGCTCTTTC TTGACTCTTG
TTTTCAGTTT CAATTCAGTG CTGTACTTGA TGACAGACAC TTCTAAATGA                    1580
AGTGCAAATT TGATACATAT GTGAATATGG ACTCAGTTTT CTTGCAGATC
AAATTTCGCG TCGTCTTCTG TATACGTCCA GGTACACTCT ATGAAGTCAA                    1680
AAGTCTACGC TCTCCTTTCT TTCTAACTCC AGTGAAGTAA TGGGGTCCTG
CTCAAGTTGA AAGAGTCCTA TTTGCACTGT AGCCTCGCCG TCTGTGAATT                    1780
GGACCATCCT ATTTAACTGG CTTCAGCCTC CCCACCTTCT TCAGCCACCT
CTCTTTTTCA GTTGGCTGAC TTCCACACCT AGCATCTCAT GAGTGCCAAG                    1880
CAAAAGGAGA GAAGAGAGAA ATAGCCTCCG CTGTTTTTA GTTTGGGGGT
TTTGCTGTTT CCTTTTATGA GACCCATTCC TATTTCTTAT AGTCAATGTT                    1980
TCTTTTATCA CGATATTATT AGTAAGAAAA CATCACTGAA ATGCTAGCTG
CAACTGACAT CTCTTTGATG TCATATGGAA GAGTTAAAAC AGGTGGAGAA                    2080
ATTCCTTGAT TCACAATGAA ATGCTCTCCT TTCCCCTGCC CCCAGACCTT
TTATCCACTT ACCTAGATTC TACATATTCT TTAAATTTCA TCTCAGGCCT                    2180
CCCTCAACCC CACCACTTCT TTTATAACTA GTCCTTTACT AATCCAACCC
ATGATGAGCT CCTCTTCCTG GCTTCTTACT GAAAGGTTAC CCTGTAACAT                    2280
GCAATTTTGC ATTTGAATAA AGCCTGCTTT TTAAGTGTTA AAAAgaattc                    2330
```

FIG. 2C

FIG. 3A

```
LAM-1    35 GWTMLCC-DFLAHHGTDCWTYHYSEKPMNWQRARRFCENDYTDLVAIQN-
FcE-R   175 GFVCNTCPEKWINFQRKC--YYPGLGTKQWVHARYACDDMEGQLVSIHS-
C-HL     75 LFPCGAQSRQWEYFEGRC--YYFSLSRMSWHKAKAECEEMHSHIIIDS-
H-MBP   118 NGIYQKCLTESLGKQVNLFFLTNGE-IMTFELVLALC-VKFQPLWPPPG-
F-PGC   452 GQDTETCDYGWHKFQGQC--YKYFAHRRTWDAAERECRLQGAHLTSILS-
HHL-1   148 GSERTCCPVNWVEHERSC--YWPSRSGKAWADADNYCRLENAHLVAVTS-
ISL      17 IFTSTAAVPQLQKALDGREYLIETLLKYNWHQAWHECARHDQQLVTIESA

LAM-1       --KAEIEYLEKTLPFSRSYYWIGIRKIG----GIMWVI-GINKSLIEEAENW
FcE-R       --PEEF--QDFLITLHASHTGSWIGLRNLDLK----GEFIWVDGSHVD----YSNW
C-HL        --YAK---QNFVMFRTRNERFWIGLTDENQE----GEWQWVDGTDTRSS---FTFW
H-MBP       --MAA---EKGAIQNLILEEAFLGMPDELTE----GQF--VDLIGNRLT---YTNW
F-PGC       --HEE---QMFVNRVGHDYQ--WIGLNDKMFE----HDFRWIDGS------TLQYENW
HHL-1       --WEEL--QKPVQHHIGPVNTWMGLHDQN----GPWKWVDGTDYE-TG--PKNW
ISL         DKNNAIIDLVKRVVGKSHNLWLGGNDEYSRDYGPFFWS--PIGQAFS--FAYW

LAM-1       GDGEPNNKKNK-----EDCVEIYIKRNKDAGK WNDDACH-KLKAAICYTI 160
FcE-R       APGEPTSRSQ------G----EDCVMM----R--GSGRWNDAFCDRKLGAWVCDR 284
C-HL        LEGEPNNR--------GFNEDCAH-----VWTSGQWNDVYCTYECYY-VCEL 203
H-MBP       NEGEPNNA--------GSDEHCVL-----LLKNGQWNDSPCF-HLPSAVCEF 245
F-PGC       RPNQPDSFFSA--G--EDCVVI----I--WHENGQWNDVPCNYHLTY-TCKK 580
HHL-1       RPEQPDDWYGHGLGGGEDCAH-----PTDDGRWNDDVCQ-RPYRWVCEI 279
ISL         SENNPNNYLHQ-----EHCVHIWNTLPLY--QWNDDDCN-VIMGYICEP 159
```

|         |     |                                    |                                   |                        |                      |     |
|---------|-----|------------------------------------|-----------------------------------|------------------------|----------------------|-----|
| LAM-1   | 173 | W S - - C S G H G E C V E I I N N - - | Y T C N C D V G Y Y G P Q C Q     |                        |                      | 205 |
| EGF     | 6   | C P L S H D G Y C L H D G V C M Y I E A L D K Y A | C N C V V G Y I G E R C Q       |                        |                      | 43  |
| F-IX    | 51  | - - C E S - - N P C L N G G S C K D D I N S - - | Y E C W C P F G F E G K N C E    |                        |                      | 83  |
| F-PGCP  | 382 | - - C K M - - N P C K N G G T C Y P T E T S - - | Y V C T C V P G Y S G D Q C E    |                        |                      | 414 |

FIG. 3B

|        |     |                                        |                              |                          |     |
|--------|-----|----------------------------------------|------------------------------|--------------------------|-----|
| LAM-1  | 207 | V I Q C E P L E A P E L G T M D C T H P L G N F N F N - S Q C A F - - - |
| LAM-1  | 269 | V I Q C E P L S A P D L G I M N C S H P L A S F S F T - S A C T F - - - |
| Ba     | 137 | A G Y C S N P G I P - I G T R K V G S Q Y R L E D - - S V - T Y - - - |
| CR1    | 694 | - - - C Q P P E I L H - G E H T P S H Q D - N F S - P G Q E V F Y - - - |
| IL-2R  | 101 | P G H C R E P P - P W E N E A T E R I Y H F V V G - Q M V Y Y Q - - - |
| F-XIII | 1   | E K P C G F P H V E N G R I A Q Y Y Y T F K S F Y F P M S I D K K L S F |

|        |     |                                    |                          |                      |     |
|--------|-----|------------------------------------|--------------------------|----------------------|-----|
| LAM-1  |     | S C S E G T N - L - T G I E E - - T T C - - E P F G N W S S P E P T C Q | 268 |
| LAM-1  |     | I C S E G T E - L - I G K K K - - T I C - - E S S G I W S N P S P I C Q | 330 |
| Ba     |     | H C S R G L T - L - R G S Q R - - R T C - - Q E G G S W S G T E P S C Q | 194 |
| CR1    |     | S C E P G Y D - L - R G A A S - - L H C - - T P Q G D W S D E A P R C A | 751 |
| IL-2R  |     | - C V Q G Y R A L H R G P A E - S V C K M T H G K T R W T Q P Q L I C T | 164 |
| F-XIII |     | F C L A G Y T T E S S R Q E E Q T T C T - T E - - W S - P E P R C F | 68  |

FIG. 3C

METHODS AND COMPOSITIONS COMPRISING ANTI-LAM-1 ANTIBODIES

This application is a division of U.S. application Ser. No. 07/983,606, filed Nov. 30, 1992, which is a continuation of U.S. application Ser. No. 07/730,503, filed Jul. 8, 1991, now abandoned, which is a continuation of U.S. application Ser. No. 07/313,109, filed Feb. 21, 1989, now abandoned. All are entitled "LYMPHOCYTE-ASSOCIATED CELL SURFACE PROTEIN.".

The invention was made with Government support and the Government has certain right in this invention under grants from the National Institutes of Health CA-34183 and AI-26872.

The invention relates to human lymphocyte-associated cell surface proteins.

BACKGROUND OF THE INVENTION

Genes exclusively expressed by one cell lineage, but not by others, often define the function of that cell population. The generation of genes by the assembly of functionally independent domains has occurred frequently as new genes have evolved to encode proteins with new functions. An inducible endothelial-leukocyte adhesion molecule (ELAM-1) is expressed on the surface of cytokine-treated endothelial cells. This molecule is thought to be responsible for the accumulation of blood leukocytes at sites of inflammation by mediating the adhesion of cells to the vascular lining (Bevilacqua et al., Proc. Natl. Acad. Sci. USA 84:9238 (1987)). A granule membrane protein found in platelets and endothelial cells, termed GMP-140, has been cloned and is homologous with ELAM-1 (Johnston et al., Blood Suppl.1 72:327A (1988)).

SUMMARY OF THE INVENTION

The invention generally features human lymphocyte-associated cell surface protein LAM-1, which includes domains homologous with binding domains of animal lectins, growth factors, and C3/C4 binding proteins; and the cDNA sequence encoding the LAM-1 protein or an immunogenic fragment of LAM-1. In a preferred embodiment, the cDNA sequence is isolated from a population of B cell-specific cDNAs from a human tonsil cDNA library, and the amino acid sequence of the protein is substantially as indicated in FIG. 2, more preferably 80% homologous with the sequence shown in FIG. 2 and most preferably 90% homologous. (Here "substantially as indicated" defines a sequence close enough to the indicated sequence to have the same function.)

In another aspect, the invention features antibody developed against lymphocyte-associated cell surface protein LAM-1, or a fragment thereof, or against a molecule that specifically associates with LAM-1, or a fragment thereof, to generate a functional molecule.

In another aspect, the invention features a method of identifying cells that express LAM-1 which involves reacting the antibody just described with a population of cells and isolating those that bind the antibody. Binding of antibody can also be used to block the receptor activity of LAM-1.

In another aspect, the invention features a method of treating a human patient suffering from a lymphocyte-mobilizing condition which involves administering a therapeutic amount of an antagonist to LAM-1 in a non-toxic pharmaceutical carrier substance. In preferred embodiments of the method the patient is suffering from tissue damage, an autoimmune disorder, or cancer, or the patient is an organ or tissue transplant recipient.

In another aspect, the invention features using the cDNA sequence defined above to isolate cross-hybridizing human DNAs.

In another aspect the invention features using LAM-1 to identify a ligand which will bind to it or to a molecule that is specifically associated with LAM-1 to generate a functional molecule.

As used herein the term antagonist includes any agent which interacts with LAM-1 and interferes with its function, eq., antibody reactive with LAM-1 or any ligand which binds to LAM-1.

Lymphocyte-associated cell surface protein LAM-1 is a unique receptor protein which has not previously been identified. LAM-1 contains domains that are homologous with those found in several different receptors and is a newly described member of a gene family that includes ELAM-1 and GMP-140, proteins which have been implicated in cell adhesion. LAM-1 most likely serves a similar function but is uniquely expressed by lymphocytes. The isolation of cDNA encoding LAM-1 has allowed the determination of the structure of this molecule; the cDNA has been used to transfer expression of LAM-1 to cells that do not express this gene.

Antibodies reactive with LAM-1 can be used to identify cells that express this receptor and to block its function. In addition, the cDNA protein product can be used to develop antagonistic ligands that can interfere with lymphocyte adhesion and function and thereby be used to treat such conditions as tissue damage and metastasis of cancer cells.

Other features and advantages of the invention will be apparent from the following description of the preferred embodiments thereof and from the claims.

In the drawings, FIG. 1A shows a restriction map of the LAM-1 cDNA clone. FIG. 1B shows a schematic model of the LAM-1 mRNA.

FIG. 3A shows the homology of LAM-1 amino acid residues 35–160 with other proteins. FIG. 3B shows the homology of LAM-1 amino acid residues 173–205 with other proteins. FIG. 3C shows the homology of LAM-1 amino acid residues 207–268 with other proteins.

B cell-specific cDNAs were isolated from a human tonsil cDNA library (ATCC #37546) using differential hybridization with labeled cDNAs derived from either B cell (RAJI) RNA or T cell (HSB-2) RNA (Tedder et al., Proc. Natl. Acad. Sci. USA 85:208–212 (1988)). Positive plaques were isolated and cloned, and the cDNA inserts were subcloned into the plasmid pSP65 (Promega, Madison, Wis.). Nucleotide sequences were determined using the method of Maxam and Gilbert (Meth. Enzymol. 65:499 (1980)). Gap penalties of –1 were assessed during homology analysis for each nucleotide or amino acid in the sequence where a gap or deletion occurred. One of the 261 RAJI+ HSB2– cDNA clones isolated, B125, contained a 1.90 kb cDNA insert that hybridized with a 2.4 kb RNA species found in several B cell lines (Tedder et al., supra). However, B125 did not hybridize with any of the other RAJI+ HSB2– clones or with mRNA from several T cell lines. The B125 cDNA clone was characterized by restriction mapping and nucleotide sequence determination. A near-full-length 2.3 kb cDNA that hybridized with B125 was isolated, sequenced, and termed pLAM-1.

As shown in FIG. 1A, a restriction map was constructed by the standard single, double or triple digestions of pLAM-1. The putative coding region is shown in black. Arrows indicate the direction and extent of nucleotide sequence determination and the open circles indicate 5'-end labeling. In FIG. 1B, a schematic model of the structure of the LAM-1 mRNA is shown. Thin lines indicate 5' and 3' untranslated sequences (UT), while the thick bar indicates the translated region. The boxes represent the lectin-like and epidermal growth factor (EGF)-like domains and the two short consensus repeat (SCR) units. The open box indicates the putative transmembrane (TM) region.

The expression of LAM-1 mRNA by cell lines of lymphoid and non-lymphoid origin was examined. Northern blot analysis revealed that LAM-1 hybridized strongly to a 2.6 kb RNA species and weakly to a 1.7 kb RNA species in poly(A)+ RNA isolated from the B cell lines Raji, SB, Laz-509, and GK-5. However, RNA isolated from two pre-B cell lines (Nalm-6, PB-697), three B cell lines (Namalwa, Daudi, BJAB), five T cell lines (CEM, Hut-78, HSB-2, Molt-15, Molt-3), a myelomonocytic cell line (U937 and U937 cultured with LPS) and erythroleukemic (K-562) cell line did not hybridize with LAM-1 suggesting that expression of this gene was preferentially associated with B lymphocytes.

The B125 cDNA clone contained an 1,181 bp open reading frame that could encode a protein of 372 amino acids as shown in FIG. 2. The numbers shown above the amino acid sequence designate amino acid residue positions. The numbers to the right indicate nucleotide residue positions. Amino acids are designated by the single-letter code, and * indicates the termination codon. The boxed sequences identify possible N-linked glycosylation sites. Hydrophobic regions that may identify signal and transmembrane peptides are underlined. The vertical arrow marks the most probable position of the amino-terminus of the mature protein. (See von Heijne, Nucleic Acids Res. 14:4683 (1986)).

The amino acid sequence of LAM-1 predicted a structure typical of a membrane glycoprotein. Two potential translation initiation sites were found at nucleotide positions 53 and 92. The second initiation site conformed best to the consensus sequence for optimal initiation (A/G)CCAUG (Kozak, Cell 44:283–292 (1986)) and was followed by a hydrophobic region of 27 amino acids that may represent a signal peptide. The algorithm of von Heijne predicted that the most probable amino-terminus of the mature protein would be the Trp at amino acid position 52. The LAM-1 sequence contained a second hydrophobic region between amino acids 346–368 which may be a transmembrane region. The deduced mature LAM-1 protein would have an extracellular region of about 294 amino acids containing 7 potential N-linked carbohydrate attachment sites. LAM-1 would have a cytoplasmic tail of 17 amino acids containing 8 basic and 1 acidic residues. The two cytoplasmic Ser residues may serve as substrates for phosphorylation since protein kinase C phosphorylates Ser residues that are on the carboxyl-terminal side of several basic residues. These results suggest that the processed LAM-1 protein would have a Mr of at least 50,000. The LAM-1 protein can be isolated by conventional techniques, such as affinity column chromatography with antibody or ligand, from cell lines that normally express this receptor or from transfected cell lines. Or the protein can be synthesized by in vitro translation of the LAM-1 cDNA.

LAM-1 combines previously unrelated domains found in three distinct families of molecules: animal lectins, growth factors, and C3/C4 binding proteins. The proposed extracellular region of LAM-1 contained a high number of Cys residues (7%) with a general structure as diagrammed in FIG. 1B. As indicated in FIG. 3, segments of homologous proteins are shown with the amino acid residue numbers at each end. Homologous amino acids are shown in boxes. Gaps (–) have been inserted in the sequences to maximize homologies. The first 157 amino acids of the protein (FIG. 3A) were homologous with the low-affinity receptor for IgE (Kikutani et al., Cell 47:657 (1986)), the asialoglycoprotein receptor (Spiess et al., Proc. Natl. Acad. Sci. USA 82:6465 (1985)) and several other carbohydrate-binding proteins (Drickamer et al., J. Biol. Chem. 256:5827 (1981); Ezekowitz et al., J. Exp. Med. 167:1034 (1988); Krusius et al., J. Biol. Chem 262:13120–13125 (1987); and Takahashi et al., J. Biol. Chem. 260:12228 (1985)). The amino acids conserved among all animal-lectin carbohydrate recognition domains are indicated (*). Although the sequence homologies were less than 30%, all the invariant residues found in animal lectin carbohydrate-recognition domains were conserved (Drickamer, J. Biol. Chem. 263:9557 (1988)).

The next domain of 36 amino acids (FIG. 3B) was homologous (36–39%) with epidermal growth factor (EGF) (Gregory, Nature 257:325 (1975)) and the EGF-like repeat units found in Factor IX (Yoshitake et al., Biochem. 25:3736 (1985)) and fibroblast proteoglycan core protein (Krusius et al., supra).

Immediately following these domains were two tandem domains of 62 amino acids each (FIG. 3C) that were homologous with the short consensus repeat units (SCR) that comprise the IL-2 receptor (Leonard et al., Nature 311:626 (1984)), Factor XIII (Ichinose et al., Biochem. 25:4633 (1986)) and many C3/C4 binding proteins (Klickstein et al., J. Exp. Med. 165:1095 (1987); and Morley et al., EMBO J. 3:153 (1984)). In contrast with all of the previously described SCR that contain four conserved Cys residues, these two SCR possessed six Cys residues. The four conserved Cys residues found in all SCR are indicated in FIG. 3C by (*); the additional conserved Cys found in LAM-1 are indicated by (+). Of the multiple SCR present in each of these proteins, the SCR with the highest homology to LAM-1 is diagrammed. A 15 amino acid spacer preceded the putative transmembrane domain.

The deduced amino acid sequence of LAM-1 is homologous with that of ELAM-1 and GMP-140. Thus these two proteins and LAM-1 define a new family of homologous structures that are expressed by different cell lineages and that can function as receptors in cellular interactions.

Use

As lymphocyte migration and infiltration into areas of tissue damage or injury or tissue transplant can cause or increase pathology, agents that impede these processes can be used for therapeutic treatment. LAM-1 can be used as an antigen to produce antibodies against this protein and to develop antagonistic ligands that can interfere with lymphocyte adhesions and function. The use of these reagents in research will permit the determination of the 3-dimensional structure of LAM-1 and clarify its role in lymphocyte function. The administration of these reagents to patients can be used to block or reduce pathology. As an example, subpopulations of malignant cells that express this antigen would allow the receptor to function in metastasis of tumor cells. Agents developed to block receptor function can inhibit the metastasis and homing of malignant cells.

Other embodiments are within the following claims.

I claim:

1. A method for inhibiting the adhesion, migration or infiltration into tissues, in inflammation, of cells that bind an antibody that binds to a human lymphocyte-associated cell surface protein having the amino acid sequence set forth in FIG. 2, wherein said method comprises the step of administering said antibody.

2. A method for blocking cellular adhesion comprising the step of contacting a population of cells that bind to an antibody that binds a human lymphocyte-associated cell surface protein having the amino acid sequence set forth in FIG. 2, with said antibody.

* * * * *